(12) United States Patent
Bozzano et al.

(10) Patent No.: US 8,052,938 B2
(45) Date of Patent: Nov. 8, 2011

(54) AROMATICS CO-PRODUCTION IN A METHANOL-TO-PROPYLENE UNIT

(75) Inventors: Andrea G. Bozzano, Northbrook, IL (US); Timur V. Voskoboynikov, Arlington Heights, IL (US); Tom N. Kalnes, LaGrange, IL (US); Paul T. Barger, Arlington Heights, IL (US); Gavin P. Towler, Inverness, IL (US); Bryan K. Glover, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/902,462

(22) Filed: Oct. 12, 2010

(65) Prior Publication Data
US 2011/0027141 A1 Feb. 3, 2011

Related U.S. Application Data

(62) Division of application No. 11/955,610, filed on Feb. 13, 2007, now Pat. No. 7,834,227.

(60) Provisional application No. 60/878,204, filed on Dec. 29, 2006.

(51) Int. Cl.
| | |
|---|---|
| *B01J 8/00* | (2006.01) |
| *B01J 8/02* | (2006.01) |
| *B01J 35/02* | (2006.01) |
| *B01J 19/00* | (2006.01) |
| *C07C 2/00* | (2006.01) |
| *C07C 2/42* | (2006.01) |
| *C07C 6/00* | (2006.01) |

(52) U.S. Cl. ......... 422/187; 422/129; 422/211; 585/312; 585/323; 585/324; 585/327; 585/467; 585/469; 585/470

(58) Field of Classification Search .................. 422/129, 422/187, 211; 585/312, 323, 324, 327, 467, 585/469, 470
See application file for complete search history.

(56) References Cited

U.S. PATENT DOCUMENTS

| | | | | |
|---|---|---|---|---|
| 4,677,242 | A * | 6/1987 | Kaiser | 585/638 |
| 4,709,115 | A * | 11/1987 | Jung et al. | 585/643 |
| 4,788,365 | A * | 11/1988 | Harandi et al. | 585/312 |
| 5,191,142 | A * | 3/1993 | Marshall et al. | 585/640 |
| 5,907,073 | A * | 5/1999 | Ghosh | 585/467 |
| 6,046,372 | A * | 4/2000 | Brown et al. | 585/640 |
| 6,506,954 | B1 * | 1/2003 | Brown et al. | 585/640 |
| 6,710,003 | B2 * | 3/2004 | Jan et al. | 502/60 |
| 7,279,608 | B2 * | 10/2007 | Ghosh et al. | 585/467 |

* cited by examiner

*Primary Examiner* — Walter Griffin
*Assistant Examiner* — Natasha Young
(74) *Attorney, Agent, or Firm* — Arthur E Gooding

(57) ABSTRACT

The present invention provides a reactor system having: (1) a first reactor receiving an oxygenate component and a hydrocarbon component and capable of converting the oxygenate component into a light olefin and the hydrocarbon component into alkyl aromatic compounds; (2) a separator system for providing a first product stream containing a $C_3$ olefin, a second stream containing a $C_7$ aromatic, and a third stream containing $C_8$ aromatic compounds; (3) a first line connecting the separator to the inlet of the first reactor for conveying the second stream to the first reactor; (4) a second line in fluid communication with the separator system for conveying the $C_3$ olefin to a propylene recovery unit, and (4) a third line in fluid communication with the separator system for conveying the $C_8$ aromatic compounds to a xylene recovery unit.

8 Claims, 1 Drawing Sheet

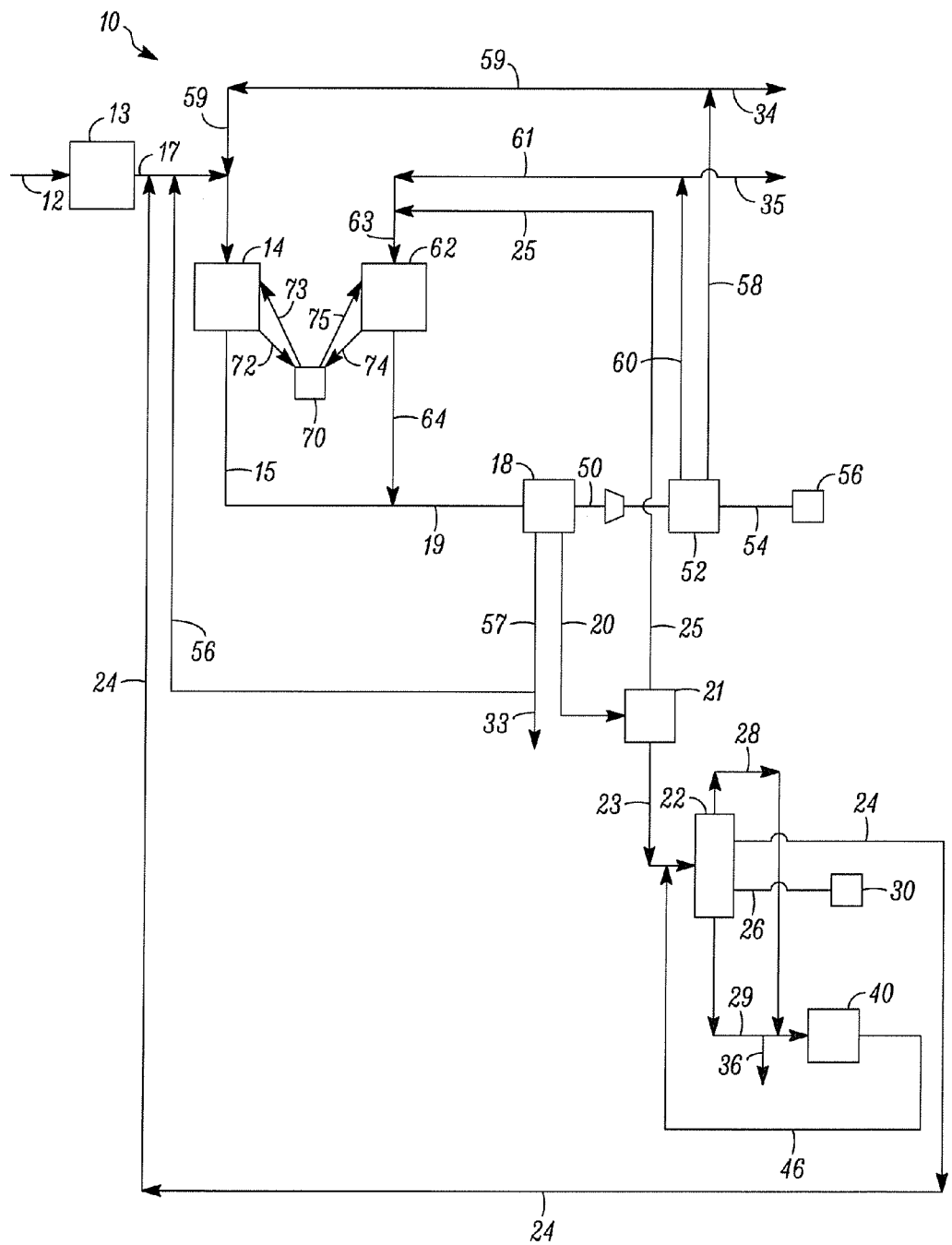

AROMATICS CO-PRODUCTION IN A METHANOL-TO-PROPYLENE UNIT

CROSS-REFERENCE TO RELATED APPLICATIONS

This application is a Division of prior copending application Ser. No. 11/955,610 filed Dec. 13, 2007, which is incorporated herein by reference in its entirety and which claims the benefit of U.S. Provisional Application No. 60/878,204 filed Dec. 29, 2006.

FIELD OF THE INVENTION

The present invention relates generally to a reactor system and a process for producing aromatics and particularly xylenes in conjunction with a methanol-to-propylene reactor system.

BACKGROUND OF THE INVENTION

A major portion of the worldwide petrochemical industry is concerned with the production of light olefin materials and their subsequent use in the production of numerous important chemical products via polymerization, oligomerization, alkylation and the like well-known chemical reactions. Light olefins include ethylene, propylene and mixtures thereof. These light olefins are essential building blocks for the modern petrochemical and chemical industries. The major source for these materials in present day refining is the steam cracking of petroleum feeds. For various reasons including geographical, economic, political and diminished supply considerations, the art has long sought a source other than petroleum for the massive quantities of raw materials that are needed to supply the demand for these light olefin materials. Thus, R & D personnel seek to use alternative feedstocks effectively and selectively to produce light olefins, thereby lessening dependence of the petrochemical industry on petroleum feedstocks. Much attention has been focused on the possibility of using hydrocarbon oxygenates and more specifically methanol or dimethylether (DME) as a prime source of the necessary alternative feedstock. Oxygenates are particularly attractive because they can be produced from such widely available materials as coal, natural gas, recycled plastics, various carbon waste streams from industry and various products and by-products from the agricultural industry. The art of making methanol and other oxygenates from these types of raw materials is well established and typically involves the use of one or more of the following procedures: (1) manufacture of synthesis gas by any of the known techniques typically using a nickel or cobalt catalyst in a steam reforming step followed by the well-known methanol synthesis step using relatively high pressure with a copper-based catalyst; (2) selective fermentation of various organic agricultural products and by-products in order to produce oxygenates; or (3) various combinations of these techniques.

Given the established and well-known technologies for producing oxygenates from alternative non-petroleum raw materials, the art has focused on different procedures for catalytically converting oxygenates such as methanol into the desired light olefin products in order to make an oxygenate to olefin (OTO) process. These light olefin products that are produced from non-petroleum based raw materials must of course be available in quantities and purities such that they are interchangeable in downstream processing with the materials that are presently produced using petroleum sources. Although many oxygenates have been discussed in the prior art, the principal focus of the two major routes to produce these desired light olefins has been on methanol conversion technology primarily because of the availability of commercially proven methanol synthesis technology. Two principal techniques are known in the art for conversion of methanol to light olefins (MTO). U.S. Pat. No. 4,387,263 discloses one MTO processes that utilizes a catalytic conversion zone containing a zeolitic type of catalyst system. The '263 patent reports on a series of experiments with methanol conversion techniques using a ZSM-5 type of catalyst system.

U.S. Pat. No. 4,587,373 discloses using a zeolitic catalyst system like ZSM-5 for purposes of making light olefins. The '373 patent discloses diverting a portion of a methanol feed stream to a DME absorption zone to allow for downsizing of a scrubbing zone.

U.S. Pat. No. 5,095,163; U.S. Pat. No. 5,126,308 and U.S. Pat. No. 5,191,141 disclose an MTO conversion technology utilizing a non-zeolitic molecular sieve catalytic material. More particularly these patents disclose using a metal aluminophosphate (ELAPO) and more specifically a silicoaluminophosphate molecular sieve (SAPO) and even more specifically SAPO-34. This SAPO-34 material was found to have a very high selectivity for light olefins with a methanol feedstock and consequently very low selectivity for the undesired corresponding light paraffins and the heavier materials.

The classical OTO technology produces a mixture of light olefins primarily ethylene and propylene along with various higher boiling olefins. Although the classical OTO process technology possesses the capability of shifting the major olefin product recovered therefrom from ethylene to propylene by various adjustments of conditions maintained in the reaction zone, the art has long sought an oxygenate to propylene (OTP) technology that would provide better yields of propylene relative to the classical OTO technology. The driving force for this shift in emphasis towards propylene is the growth rate of the propylene market versus the growth rate of the ethylene market. The existing sources of propylene production in the marketplace are primarily based on conventional steam cracking of naphtha, LPG streams, propane streams and the like. Another principal source of propylene is produced in a fluid catalytic cracking (FCC) hydrocarbon conversion process in the modern day refinery.

US 2003/0139635A1 discloses a fixed bed methanol to propylene (MTP) process for selectively producing propylene from a feedstock of methanol and/or DME. This patent application discloses a flowscheme having an oxygenate to propylene (OTP) synthesis portion having three reactors in a parallel flow arrangement with respect to the oxygenate feed and utilize a steam diluent and fixed beds of oxygenate conversion catalysts. The reactors are connected in a serial flow arrangement with respect to the effluents of the first reactor and the second reactor.

EP-B-1025068 discloses using two reaction zones to convert an oxygenate feed and a by-product fraction containing $C_4^+$ hydrocarbons to ethylene and propylene. This patent discloses that the two reaction zones allow for independent selection of catalyst and conversion conditions for each zone. This patent discloses using a non-zeolitic molecular sieve catalyst such as SAPO-34 for an oxygenate to light olefin reaction zone and either a non-zeolitic molecular sieve catalyst or a zeolitic catalyst such as ZSM-5 material for the auxiliary reaction zone which operates to convert the $C_4^+$ by-product fraction to the desired light olefin (i.e., $C_2$ and $C_3$ olefins). The patent discloses using a circulating fluid bed or a riser reaction for the first reaction zone and a fluid bed or a fixed bed or a fixed tube reactor for the second reaction zone.

SUMMARY OF THE INVENTION

The present invention provides a reactor system having: (1) a first reactor having an inlet, an outlet and a reaction zone, the first reactor is capable of receiving a feed stream having an oxygenate component and a hydrocarbon component and of converting a portion of the oxygenate component to a light olefin and alkylating a portion of the hydrocarbon component to form alkyl aromatic compounds, the light olefin and the alkyl aromatic compounds are included in a first effluent stream; (2) a separator system in fluid communication with the outlet of the first reactor for receiving the first effluent stream of the first reactor and for providing a first product stream containing a $C_3$ olefin, a second stream containing a $C_7$ aromatic, and a third stream containing $C_8$ aromatic compounds; (3) a first line connecting the separator to the inlet of the first reactor for conveying the second stream to the first reactor; (4) a second line in fluid communication with the separator system for conveying the $C_3$ olefin to a propylene recovery unit, and (4) a third line in fluid communication with the separator system for conveying the $C_8$ aromatic compounds to a xylene recovery unit.

The present invention further provides a process for converting an oxygenate feed to propylene ($C_3$ olefin) and a hydrocarbon feed to alkyl substituted benzene compounds. The process includes: (1) reacting in a reaction zone the oxygenate feed in the presence of a molecular sieve catalyst to convert a portion of oxygenate compounds in the oxygenate feed to a $C_3$ olefin; (2) reacting in the reaction zone the hydrocarbon feed in the presence of the molecular sieve catalyst to form $C_6^+$ compounds; (3) forming an effluent stream containing the $C_3$ olefin and the $C_6^+$ compounds; (4) separating a portion of the effluent stream in a separation zone into a first stream rich in the $C_3$ olefin, a second stream rich in $C_7$; (5) passing the first stream to a first storage unit; and (6) recycling the second stream to an inlet of the reaction zone.

The present invention further provides a process for preparing xylenes. The process includes: (1) providing a first stream containing aromatic compounds under pressure to a first reactor, the first reactor being operated under conditions for converting an oxygenate compound to a $C_3$ olefin, the first reactor containing a molecular sieve type catalyst; (2) alkylating a portion of the first stream in the first reactor to form an effluent stream rich in $C_6^+$ aromatic compounds; (3) separating a portion of the effluent stream in a separation zone into a first stream rich in a $C_7$ aromatic compound and into a second stream rich in $C_8$ aromatic compounds; (4) recycling the first stream to an inlet of the first reactor; (5) and passing the second stream to a recovery unit.

BRIEF DESCRIPTION OF THE DRAWING

The FIGURE is a schematic view of a reactor system for recycling $C_7$ aromatic compounds to an oxygenate to propylene reactor system and for producing and isolating $C_8$ aromatic compounds (xylenes).

TERMS AND CONDITIONS DEFINITIONS

The following terms and conditions are used in the present specification with the following meanings (1) A "portion" of a stream means either an aliquot part that has the same composition as the whole stream or a part that is obtained by eliminating a readily separable component therefrom (e.g., if the stream contains hydrocarbons in admixture with steam, then after condensation of a major portion of the steam, it comprises an aqueous portion and a hydrocarbon portion); (2) the presence of necessary compressors and/or pumps is understood when flow is shown from a zone of relatively low pressure to a zone of higher pressure; (3) the presence of necessary heating and/or cooling means is implied when flow is shown between zones operating at different temperatures; (4) the term "light olefins" means ethylene, propylene and mixtures thereof; (5) the term "heavy olefin" means an olefin having a molecular weight greater than propylene; (6) the expression "OTP" process means a process for converting an oxygenate to propylene and in a preferred embodiment when the oxygenate is methanol the OTP process is referred to as an "MTP" process herein; (7) the term "oxygenate" means an oxygen-substituted aliphatic hydrocarbon containing 1 to 10 carbon atoms include aliphatic alcohols, ethers, and carbonyl compounds (e.g., aldehydes, ketones, carboxylic acids, and the like) and mixtures of these materials; (8) the term "highly unsaturated hydrocarbon" means a hydrocarbon which contains two or more double bonds or a triple bond in its structure; (9) the term "fluidized bed" means particles of a catalyst are entrained in a pressurized stream of gas or liquid; (10) the term $C_x^+$ refers to a hydrocarbon compound having x number of carbon atoms or greater and the number x can equal anywhere from 2 to 30 carbons; and (11) the term "purge" and as referenced in the FIGURE is for removing water, paraffins and unwanted or unreactive compounds as is well known to those skilled in the art.

DETAILED DESCRIPTION OF THE INVENTION

The following description of a preferred embodiment of the process of the present invention is made with reference to the attached FIGURE. In the interest of simplifying the description of the invention in order to facilitate understanding the FIGURE do not contain representations of heaters, heat exchangers, coolers, valves, control means and other conventional items that are well known to those of ordinary skill in the chemical engineering art except where their presence is essential to the understanding of the present invention.

The FIGURE shows a reactor system 10 for co-producing xylenes with propylene from an oxygenate-containing hydrocarbon feed stream 11 in an OTP reactor 14 having an effluent stream 15. The reactor system 10 has a separator unit having a first stage 18 for separating $C_6^+$ aromatic hydrocarbons from light and heavy olefins. The $C_6^+$ aromatic hydrocarbons are part of an effluent stream 20 and are directed through an optional steam stripper 21, which concentrates the $C_6^+$ aromatic hydrocarbons and removes a portion of the heavy olefins overhead, and the heavy olefins are removed and transferred through line 25 to an olefin interconversion reactor 62. From the steam stripper, line 23 carries the $C_6^+$ aromatic hydrocarbons to a second stage 22 where the $C_6^+$ aromatic hydrocarbons are separated in a distillation column or a series of distillation columns into a first effluent stream 24 rich in $C_7$, a second effluent stream 26 rich in $C_8$, a third effluent stream 28 rich in $C_6$ and a fourth effluent stream 29 rich in $C_9^+$ aromatic compounds. A portion of the $C_9^+$ aromatic compounds in line 29 may be purged in line 36. The first effluent stream 24 is recycled back to join stream 17 and form part of the feed stream 11. The second effluent stream 26 is directed to a xylene recovery unit 30. The third effluent stream 28 merges with the fourth effluent stream 29 and the combined flow is directed to a second reactor 40 for performing transalkylating reactions.

The light and heavy olefins form part of an effluent stream 50 that is directed from the separator 18 after compression to an olefin separation unit 52 where $C_3$ olefin (propylene) is separated from lighter and heavier olefins and passed through effluent line 54 to a propylene recovery unit 56. The $C_2$ olefin forms part of an effluent line 58. $C_2$ olefin product can be recovered in line 34. The remaining $C_2$ olefin is recycled back in stream 59 to join stream 17 and form part of the feed stream 11. The $C_4^+$ olefins ($C_4$-$C_8$) are passed through line 60 from which a portion of the $C_4^+$ olefins may be recovered through line 35. The remaining $C_4^+$ olefins are passed through line 61 to join heavy olefins in line 25 via line 63. The heavy olefins and $C_4^+$ olefins in line 63 are passed to a third reactor which is the olefin interconversion reactor 62 in which a portion of the $C_4^+$ olefins are converted to $C_3$ olefins which form part of an effluent stream 64 and are directed back to and inlet of the separator 18. Water is recycled back to the first reactor 14 through lines 57 and 56 and a portion of the water can also be purged through line 33.

The first reactor 14 converts oxygenate to propylene and is known in the art as an OTP reactor. In a preferred form of the OTP reactor 14, the oxygenate-containing hydrocarbon feed is catalytically and selectively converted to propylene and by-product hydrocarbons containing aliphatic moieties such as—but not limited to—methane, ethane, ethylene, propane, butylene, butane and limited amounts of other higher carbon number aliphatics by contacting the feedstock with an OTP catalyst at effective OTP conditions. The oxygenate feed stream 11 will contain, in a preferred form of the invention, one, some or all of methanol, dimethyl ether (DME), ethanol, diethyl ether, methylether, formaldehyde, dimethyl ketone, acetic acid, and mixtures thereof. In a most preferred form of the invention, the oxygenate feed stream 11 will contain methanol or dimethylether or mixtures thereof. A fresh oxygenate feed stream 12 can be first conveyed to an optional reactor 13 for converting at least a portion of the methanol to dimethyl ether and an effluent stream 17 of the oxygenate feed stream is then conveyed with other streams into the first reactor 14 via the oxygenate feed stream 11.

A diluent is not absolutely required in the first reactor 14 but is a useful option to maintain the selectivity of the OTP catalyst to produce light olefins, particularly propylene. The use of a diluent such as steam can provide certain equipment cost and thermal efficiency advantages as well as lowering the partial pressure of the oxygenate reactants, thereby increasing selectivity to olefins. The phase change between steam and liquid water can also be employed to advantage in transferring heat between the feedstock and the reactor effluent, and the separation of the diluent from the product requires only a simple condensation step to separate water from the light olefin products.

A diluent is thus preferably used in the OTP reactor 14 to control partial pressure of the oxygenate reactant to provide a heat sink for the net exothermic reactions occurring therein and to shift the overall reaction selectivity towards propylene. Suitable diluents for use in the reaction zones include helium, argon, nitrogen, carbon monoxide, carbon dioxide, hydrogen, water, $C_1$-$C_5$ paraffins, aromatic hydrocarbons and mixtures of these materials. Preferred diluents are steam, methane, an aromatic compounds, and mixtures thereof. Preferred diluents are relatively inert at the conditions maintained in the reaction zones. An especially preferred diluent is steam since it is relatively easily recovered from the effluent stream utilizing condensation techniques. The amount of diluent used will be selected from the range of 0.1:1 to 12:1 and more typically from about 0.1:1 to 5:1 moles of diluent per mole of oxygenate in order to lower the partial pressure of the oxygenates to a level which favors production of propylene. In a preferred form of the present invention and as described above, the reactor 14 will be supplied with a portion of an ethylene-rich by-product stream 58 and a $C_7$ rich stream 24. The $C_2$ olefin recycle stream and the $C_7$ rich stream 24 will thus furnish a hydrocarbon diluent to a reaction zone of the reactor 14 and therefore the amount of diluent that must be added to achieve the target diluent to oxygenate mole ratio will diminish once the reaction zone is started up and $C_2$ and the $C_7$ rich stream 24 recycle stream is initiated.

The conversion conditions used in the reactor 14 is carefully chosen to favor the production of propylene from the oxygenate components of the oxygenate-containing hydrocarbon feed stream 11. In a preferred form of the invention, oxygenate conversion temperatures will be from about 350° to about 600° C. The lower portion of this oxygenate conversion temperature range with certain catalysts is known to favor the production of propylene with the upper portion favoring the production of ethylene at the expense of propylene. Preferred inlet temperatures into the reaction zones are therefore in the range of 350° to 500° C., more preferably in the range of about 375° to 500° C. and most preferably in the range of 375° to 475° C.

These reaction conditions have been found to also be effective in alkylating aromatic compounds to form $C_8$ compounds (xylenes). Thus, the oxygenate-containing hydrocarbon feed stream further includes aromatic components $C_5^+$ that are alkylated to form $C_6$ and $C_6^+$ hydrocarbon compounds, and, therefore alkylated aromatic compounds can be produced at the same time that oxygenates are being converted to propylene.

These reactions are carried out in the presence of a catalyst and more preferably a molecular sieve catalyst. The catalyst is contacted with the feed stream 11 in the reactor using a fluidized bed, moving bed or batch type catalyst distribution systems. In one preferred form of the invention the reactor 14 will contain a moving bed catalyst system.

Suitable catalysts include zeolitic molecular sieves in the calcined form be represented by the general formula:

$$Me_{2/n}O:Al_2O_3:xSiO_2:yH_2O$$

where Me is a cation, x is the framework $SiO_2$ to $Al_2O_3$ ratio and has a value from about 2 to infinity, n is the cation valence and y has a value of about 2 to 100 or more and more typically about 2 to 25.

Zeolites which may be used include chabazite—also referred to as Zeolite D, clinoptilolite, erionite, ferrierite, mordenite, Zeolite A, Zeolite P, ZSM-5, ZSM-11, and MCM-22. Zeolites having a high silica content (i.e., those having framework silica to alumina ratios greater than 100 and typically greater than 150 with good results achieved at a silica to alumina mole ratio of about 150:1 to 800:1) are especially preferred. One such high-silica-content zeolite having the structure of ZSM-5 is silicalite, as the term used herein includes both the silicapolymorph disclosed in U.S. Pat. No. 4,061,724 and also the F-silicate disclosed in U.S. Pat. No. 4,073,865. Best results are obtained with ZSM-5 or ZSM-11 or a mixture thereof. Such catalyst are sometimes referred to as having a "pentasil-type" structure.

Suitable non-zeolitic molecular sieves are embraced by an empirical chemical composition, on an anhydrous basis, expressed by the empirical formula:

$$(EL_xAl_yP_z)O_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of aluminum and is at least 0.01, z is the mole fraction of phosphorous and is at least 0.01 and x+y+z=1. When EL is a mixture of metals, x represents the total amount of the element mixture present. Preferred elements (EL) are silicon, magnesium and cobalt with silicon being especially preferred.

It is contemplated using blends of zeolitic-type catalyst, blends of non-zeolitic molecular sieve catalysts and blends of both zeolitic-type and non-zeolitic-type molecular sieve catalyst.

The second reactor 40 is operated under conditions to transalkylate $C_6$ (benzene) and $C_6^+$ aromatic compounds and under conditions to optimize the production of $C_8$ aromatics. The $C_6^+$ aromatic compounds include benzene, alkyl substituted benzenes including methyl benzene (toluene), dimethyl benzenes (xylenes), trimethyl benzenes, tetramethyl benzenes, and $C_2$-$C_6$ alkyl substituted benzenes. The $C_8$ aromatics are directed to a first effluent stream 26 and are passed to the xylene recovery unit 30. The $C_8$ aromatics include o-xylene, m-xylene and p-xylene and most preferably p-xylene. The second reactor 40 forms a second effluent stream 46 rich in $C_7$ aromatics which are recycled back to the separator 22.

To effect a transalkylation reaction, the present invention incorporates a transalkylation catalyst in at least one zone, but no limitation is intended in regard to a specific catalyst other than size and shape. Conditions employed in the transalkylation zone normally include a temperature of from about 200° to about 540° C. The transalkylation zone is operated at moderately elevated pressures broadly ranging from about 100 kPa to about 6 MPa absolute. The transalkylation reaction can be effected lover a wide range of space velocities, with higher space velocities effecting a higher ratio of para-xylene at the expense of conversion. Weighted hourly space velocity (WHSV) generally is in the range of from about 0.1 to about 20 $hr^{-1}$.

The transalkylation effluent is separated into a light recycle stream, a mixed $C_8$ aromatics product and a heavy-aromatics stream. The mixed $C_8$ aromatics product can be sent for recovery of para-xylene and other valuable isomers. The light recycle stream may be diverted to other uses such as to benzene and toluene recovery, but alternatively is recycled partially to the transalkylation zone. The heavy recycle stream contains substantially all of the $C_9$ and heavier aromatics and may be partially or totally recycled to the transalkylation reaction zone.

One skilled in the art is familiar with several types of transalkylation catalysts that may be suitably sized and shaped for use in the present invention. For example, in U.S. Pat. No. 3,849,340, which is herein incorporated by reference, a catalytic composite is described comprising a mordenite component having a $SiO_2/Al_2O_3$ mole ratio of at least 40:1 prepared by acid extracting $Al_2O_3$ from mordenite prepared with an initial $SiO_2/Al_2O_3$ mole ratio of about 12:1 to about 30:1 and a metal component selected from copper, silver and zirconium. Friedel-Crafts metal halides such as aluminum chloride have been employed with good results and are suitable for use in the present process. Hydrogen halides, boron halides, Group I-A metal halides, iron group metal halides, etc., have been found suitable. Refractory inorganic oxides, combined with the above-mentioned and other known catalytic materials, have been found useful in transalkylation operations. For instance, silica-alumina is described in U.S. Pat. No. 5,763,720. Crystalline aluminosilicates have also been employed in the art as transalkylation catalysts. ZSM-12 is more particularly described in U.S. Pat. No. 3,832,449. Zeolite beta is more particularly described in Re. 28,341. A favored form of zeolite beta is described in U.S. Pat. No. 5,723,710. The preparation of MFI topology zeolite is also well known in the art. In one method, the zeolite is prepared by crystallizing a mixture containing an alumina source, a silica source, an alkali metal source, water and an alkyl ammonium compound or its precursor. Further descriptions are in U.S. Pat. No. 4,159,282; U.S. Pat. No. 4,163,018 and U.S. Pat. No. 4,278,565.

A refractory binder or matrix is optionally utilized to facilitate fabrication of the catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, phosphate, zinc oxide and silica. Alumina is a preferred binder.

The catalyst also contains an optional metal component. One preferred metal component is a Group VIII (IUPAC 8-10) metal, preferably a platinum-group metal. Alternatively a preferred metal component is rhenium. Of the preferred platinum group, i.e., platinum, palladium, rhodium, ruthenium, osmium and iridium, and platinum is especially preferred. This component may exist within the final catalytic composite as a compound such as an oxide, sulfide, halide, or oxyhalide, in chemical combination with one or more of the other ingredients of the composite, or, preferably, as an elemental metal. This component may be present in the final catalyst composite in any amount which is catalytically effective, generally comprising about 0.01 to about 2 mass-% of the final catalyst calculated on an elemental basis. The platinum-group metal component may be incorporated into the catalyst in any suitable manner such as coprecipitation or cogellation with the carrier material, ion exchange or impregnation. Impregnation using water-soluble compounds of the metal is preferred. Typical platinum-group compounds which may be employed are chloroplatinic acid, ammonium chloroplatinate, bromoplatinic acid, platinum dichloride, platinum tetrachloride hydrate, tetraamine platinum chloride, tetraamine platinum nitrate, platinum dichlorocarbonyl dichloride, dinitrodiaminoplatinum, palladium chloride, palladium chloride dihydrate, palladium nitrate, etc. Chloroplatinic acid is preferred as a source of the especially preferred platinum component. Moreover, when the metal component is rhenium, typical rhenium compounds which may be employed include ammonium perrhenate, sodium perrhenate, potassium perrhenate, potassium rhenium oxychloride, potassium hexachlororhenate (IV), rhenium chloride, rhenium heptoxide, and the like compounds. The utilization of an aqueous solution of perrhenic acid is highly preferred in the impregnation of the rhenium component Rhenium may also be used in conjunction with a platinum-group metal.

The third reactor 62, in a preferred form of the invention, is an interconversion reactor capable of converting non-propylene hydrocarbons having fewer than three carbon atoms or four carbon atoms or greater, for example $C_4$-$C_8$ hydrocarbons, into propylene The third reactor 62 preferably utilizes the same catalyst as used in the first reactor 14 and contacts feed stream 60 to the catalyst using a moving bed, fluidized bed, or batch type reactor systems. Also, in a preferred form of the invention, the first reactor and the third reactor share a catalyst regenerator system 70 connected to the first reactor through line 72 and the third reactor through line 74. Regenerated catalyst lines 73 and 75 return regenerated catalyst to reactors 14 and 62, respectively. An effluent from the third reactor 62 is transferred through the line 64 to an inlet of the separator 18 via line 19.

A diluent may be used in the interconversion reactor 62 to control the partial pressure of the heavy olefin reactant used therein and to provide an additional heat source for the endothermic interconversion reaction. Suitable diluents can be chosen from those previously set forth in connection with the operation of the OTP reaction zones. Of these preferred diluents, steam involves the risk of hydrothermal deactivation of the catalyst used in the interconversion reactor if steam is used in high concentration but is typically used because of its ability to control and/or prevent coke formation in heaters, heat exchangers and reactor internals, its ready availability, its ease of separability from the products of the interconversion reaction and because it can be used at a much lower concentration than in the OTP reaction zones. The amount of diluent preferably used in the interconversion reaction zone corresponds 0.001:1 to 1:1 moles of diluent per mole of $C_4^+$ olefin charged to this zone and more preferably to a mole ratio of 0.01:1 to 0.5:1. Unlike the situation with respect to the OTP reaction zones it is to be noted that since $H_2O$ is not a by-product of the $C_4^+$ interconversion reactions performed in the interconversion reactor, there is typically no net make of diluent across this zone so that the effective amount of diluent used in the interconversion reactor is the amount charged thereto. However, it is within the scope of the present invention to charge some oxygenate to the interconversion reactor in an amount sufficient to off-set the endothermic interconversion reactions arising therein.

One preferred form of the present invention utilizes moving bed technology in the OTP reactor 14 and the olefin interconversion reactor 62 to enhance the selectivity of the overall process for propylene production. The use of moving bed technology in a classical MTO process is known and is shown in U.S. Pat. No. 5,157,181.

Moving bed reaction zones for use in the instant invention can be configured in a number of ways, for example, the catalyst particles can be introduced to an upper section of the OTP reaction zones and fed by gravity through the entire volume of the reaction zones, wherein the dual-function catalyst is contacted, in a preferred form of the invention, a radially flowing feed stream; thus, the fluid stream or streams flow transversely to the direction of flow of the catalyst. It is contemplated, that the feed streams or by-product stream could be directed to flow in a countercurrent direction to the catalyst movement or in a concurrent direction without departing from the scope of the present invention.

More typically the catalyst particles are introduced into an annular catalyst chamber, or annular catalyst chambers, defined by concentric catalyst retaining screens that run through the reactors wherein the catalyst particles travel down through the annular catalyst chamber and are withdrawn from a lower section of these reaction zones.

During the traversal through the reactors, a carbonaceous material, i.e., coke, is deposited on the catalyst as it flows through the reactors. The carbonaceous deposit material has the effect of reducing the number of active sites on the catalyst which thereby affects the extent of the overall conversion and the selectivity to propylene. A portion of the coked catalyst is thus withdrawn from the reactors and regenerated in station 70 to remove at least a portion of the coke therefrom. In a preferred form of the invention where the same catalyst is used in the first reactor 14 and the third reactor 62 coked particles from both reactors can be mixed together and charged to the common regeneration station 70. It is within the scope of the present invention to charge at least a portion of the partially coked catalyst particles withdrawn from the third reactor to the first OTP reactor. This can be advantageous when the selectivity of the catalyst to propylene in the first reactor is improved due to the partial coverage of active sites with fresh coke deposits.

The carbonaceous material is removed from the catalyst by oxidative regeneration wherein a moving bed of the catalyst particles withdrawn from the reactors is contacted with an oxygen-containing gas stream at sufficient temperature and oxygen concentration to allow the desired amount of the carbonaceous materials to be removed by combustion from the catalyst.

Both the oxygenate to propylene conversion and the $C_4^+$ olefin interconversion steps are effectively carried out over a wide range of pressures including inlet total pressures between about 0.1 atm (10.1 kPa) up to about 100 atm (10.1 MPa) but it is well known that the formation of lighter olefins like propylene are favored at low pressure conditions. It is thus preferred for both of these steps to use an inlet pressure in the range of about 1 to 4 atm (101.3 to 405 kPa) and best results are achieved at about 1.4 to about 3.4 atm (138 to 345 kPa).

The contact time of the reactants with the catalyst is ordinarily measured in relative terms of a Weight Hourly Space Velocity (WHSV) which is calculated for the OTP conversion step on the basis of mass hourly flow rate of the sum of the mass of oxygenate reactants passed to the OTP reaction zone plus the mass of any reactive hydrocarbon material present in the feed stream or any of the recycle streams passed to the first reaction zone divided by the mass of the dual-function catalyst present in the reaction zone. The WHSV for the $C_4^+$ olefin interconversion step is likewise calculated on the basis of mass hourly flow rate of the sum of the mass of $C_4^+$ olefin by-product stream passed thereto plus the mass of any reactive hydrocarbons present in any recycle stream or diluent stream passed thereto divided by the mass of the catalyst present in the third reactor 62. Those skilled in the art will recognize that the contact time of the reactants with the catalyst is proportional to the inverse of the WHSV such that as the WHSV increases contact time decreases and conversely a decrease in WHSV produces an increase in contact time. WHSV for use in both the OTP reactors and the interconversion reactor associated with the present invention can range from about 0.1 to 100 $hr^{-1}$, with a preferred range being about 0.5 to 20 $hr^{-1}$, with best results ordinarily attained in the range of 0.5 to 10 $hr^{-1}$.

The present invention further includes an optional selective hydrogenation treatment step to selectively hydrogenate highly unsaturated hydrocarbons such as dienes and/or acetylenic hydrocarbons that are formed in the OTP conversion step in minor amounts (i.e., less than 2 wt-% of the amount of oxygenate feed converted and typically about 0.01 to 1 wt-% of the amount converted). While these highly unsaturated hydrocarbons do not represent a substantial source of propylene yield loss, it has been found that they are a very significant contributor to the rate of coke deposition on the preferred catalyst. The selective hydrogenation conditions utilized in this treatment step are selected from conditions known to those of skill in the art to be effective to convert highly unsaturated hydrocarbons to the corresponding olefins while minimizing or eliminating any over-hydrogenation to the corresponding fully saturated hydrocarbon.

EXAMPLE 1

A pilot plant test was conducted using a methanol and ethylene feed stream having 30.4 g/hr methanol, 4.8 g/hr of ethylene and 15.0 g/hr of water. The plant was operated at 440° C. at an inlet, under a pressure of 76 kPa (11 psig) at the inlet a GHSV of 6,100 $hr^{-1}$. The feed stream was contacted with a ZSM-5 catalyst. A product was collected from the plant and was found to have by weight on a dry basis 25.3% propylene, 32.2% ethylene, 0.38% benzene, 0.38% toluene, 1.37% xylenes and 0.68% of $C_9^+$.

EXAMPLE 2

A second pilot plant test was conducted using a feed stream having by weight 30.5 g/hr methanol, 15.0 g/hr; water, 4.2 g/hr ethylene and 50.9 g/hr heavy hydrocarbons. The heavy hydrocarbons comprised by weight approximately 25% $C_5$, 12.5% hexene, 25% toluene, 12.5% octenes and 25% trimethyl benzenes. Hence the combined feed contained 19.4% toluene and 19.4% $C_9$ aromatics by weight on a dry basis. The pilot plant reactor was operated at 440° C. at an inlet, under a pressure of 122 kPa (17.7 psig) at the inlet a GHSV of 6,100 $hr^{-1}$. ZSM-5 catalyst was used as in Example 1. An effluent from the reactor was collected and analyzed to have by weight on a dry basis 12.2% propylene, 5.12% ethylene, 0.4% benzene, 13.6% toluene, 7.6% xylene and 22.3% $C_9^+$. Example 2 shows an increased selectivity over Example 1 in terms of xylene and $C_9$ aromatics while showing a disappearance of toluene.

The invention claimed is:

1. A reactor system comprising:
a first reactor having an inlet, an outlet and a reaction zone, the first reactor is capable of receiving a feed stream having an oxygenate component and a hydrocarbon component and of converting a portion of the oxygenate component to a light olefin and alkylating a portion of the hydrocarbon component to form alkyl aromatic compounds, the light olefin and the alkyl aromatic compounds are included in a first effluent stream;
a separator system in fluid communication with the outlet of the first reactor for receiving the first effluent stream of the first reactor and for providing a first product stream containing a $C_3$ olefin, a second stream containing a $C_7$ aromatic, and a third stream containing $C_8$ aromatic compounds;
a first line connecting the separator system to the inlet of the first reactor for conveying the second stream to the first reactor;
a second line in fluid communication with the separator system for conveying the $C_3$ olefin to a propylene recovery unit; and
a third line in fluid communication with the separator system for conveying the $C_8$ aromatic compounds to a xylene recovery unit.

2. The reactor system of claim 1 further comprising a second reactor for receiving a $C_6^+$ aromatic hydrocarbon containing feed stream from the separator system and subjecting the feed stream to conditions for transalkylating the $C_6^+$ aromatic hydrocarbon to form an effluent stream rich in $C_8$ hydrocarbons.

3. The reactor system of claim 1 further comprising a third reactor for receiving a $C_{4+}$ olefin stream from an outlet of the separator system and forming an effluent stream rich in $C_3$.

4. The reactor system of claim 3 wherein the effluent stream rich in $C_3$ from the third reactor is in fluid communication with an inlet of the separator system.

5. The reactor system of claim 3 further comprising a catalyst regeneration unit in fluid communication with both the first reactor and the third reactor.

6. The reactor system of claim 1 wherein the oxygenate component is selected from the group consisting of methanol and dimethyl ether.

7. The reactor system of claim 1 further comprising a first catalyst chamber in the first reactor for guiding a flow of a catalyst material through a portion of the first reactor.

8. The reactor system of claim 1 further comprising a steam stripper in fluid communication with the first line for concentrating the aromatic components of the second feed stream.

* * * * *